(12) United States Patent
Kalia et al.

(10) Patent No.: US 11,049,613 B2
(45) Date of Patent: Jun. 29, 2021

(54) SECURITY SCANNING FOR PASSENGERS WITH MEDICAL DEVICES

(71) Applicant: International Business Machines Corporation, Armonk, NY (US)

(72) Inventors: Anup Kalia, Yorktown Heights, NY (US); Clifford A. Pickover, Yorktown Heights, NY (US); Valentina Salapura, Yorktown Heights, NY (US); Maja Vukovic, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 290 days.

(21) Appl. No.: 15/843,125

(22) Filed: Dec. 15, 2017

(65) Prior Publication Data

US 2019/0189274 A1    Jun. 20, 2019

(51) Int. Cl.
*G16H 40/67* (2018.01)
*H04L 9/32* (2006.01)
(Continued)

(52) U.S. Cl.
CPC ............ *G16H 40/67* (2018.01); *A61B 5/073* (2013.01); *A61B 5/14503* (2013.01); *A61F 2/02* (2013.01); *A61F 5/445* (2013.01); *A61N 1/08* (2013.01); *A61N 5/1001* (2013.01); *G07C 9/25* (2020.01); *H04L 9/3226* (2013.01); *H04W 12/06* (2013.01); *A61B 5/14532* (2013.01); *A61B 5/686* (2013.01);
(Continued)

(58) Field of Classification Search
CPC .... G16H 40/67; A61B 5/073; A61B 5/14503; A61B 5/14532; A61B 5/686; A61B 2562/028; A61B 2562/08; A61F 5/445; A61F 2002/183; A61F 2250/0002; A61N 1/08; G07C 9/00071; H04L 9/3226; H04L 2209/80; H04L 2209/88; H04W 12/06; G06F 19/30; G06F 19/32; G06F 19/34; G06F 19/3418; G06Q 2220/00; G06Q 50/22; G06Q 50/24
See application file for complete search history.

(56) References Cited

U.S. PATENT DOCUMENTS

| 5,629,678 | A | * | 5/1997 | Gargano | ............... | A61B 5/0031 128/903 |
| 7,218,232 | B2 | * | 5/2007 | DiSilvestro | ............ | A61B 90/98 340/572.8 |

(Continued)

FOREIGN PATENT DOCUMENTS

WO    WO 03/095024 A2    11/2003

OTHER PUBLICATIONS

Medtronic, Inc., "Heart Failure Pacemaker with Defibrillation Patient Manual," Jun. 29, 2012, pp. 19-21, 82-84. (Year: 2012).*
(Continued)

*Primary Examiner* — Elaine Gort
*Assistant Examiner* — Amanda R. Covington
(74) *Attorney, Agent, or Firm* — Anthony Curro, Esq.; McGinn I.P. Law Group, PLLC.

(57) ABSTRACT

A security scanning method, system, and computer program product, includes receiving a communication of information from a medical device associated with a traveler via a security device and triggering a sending of the information to the device and storing the information in a blockchain.

18 Claims, 4 Drawing Sheets

(51) Int. Cl.
  *A61F 2/02* (2006.01)
  *A61B 5/07* (2006.01)
  *A61F 5/445* (2006.01)
  *H04W 12/06* (2021.01)
  *A61N 1/08* (2006.01)
  *A61F 2/18* (2006.01)
  *A61B 5/00* (2006.01)
  *A61B 5/145* (2006.01)
  *A61N 5/10* (2006.01)
  *G07C 9/25* (2020.01)

(52) U.S. Cl.
  CPC ..... *A61B 2562/028* (2013.01); *A61B 2562/08* (2013.01); *A61F 2002/183* (2013.01); *A61F 2250/0002* (2013.01); *G06Q 2220/00* (2013.01); *H04L 2209/80* (2013.01); *H04L 2209/88* (2013.01)

(56) References Cited

U.S. PATENT DOCUMENTS

| | | | | |
|---|---|---|---|---|
| 8,015,024 | B2* | 9/2011 | DiSilvestro | A61B 5/076 |
| | | | | 705/2 |
| 9,749,140 | B2 | 8/2017 | Oberhauser et al. | |
| 9,998,286 | B1* | 6/2018 | Ramathal | G06Q 10/10 |
| 2007/0018810 | A1* | 1/2007 | Smythe | A61B 5/0031 |
| | | | | 340/539.12 |
| 2007/0232884 | A1* | 10/2007 | Maschke | A01K 11/006 |
| | | | | 600/407 |
| 2011/0187535 | A1* | 8/2011 | Crowley | G08B 23/00 |
| | | | | 340/573.1 |
| 2014/0257849 | A1* | 9/2014 | Richards | G06F 19/3418 |
| | | | | 705/3 |
| 2015/0332283 | A1* | 11/2015 | Witchey | G06F 21/00 |
| | | | | 705/3 |
| 2015/0358763 | A1* | 12/2015 | Mazar | H04B 1/385 |
| | | | | 455/41.2 |
| 2017/0091397 | A1* | 3/2017 | Shah | H04L 63/107 |
| 2017/0150939 | A1* | 6/2017 | Shah | A61B 6/548 |
| 2017/0222814 | A1* | 8/2017 | Oberhauser | H04L 9/3247 |
| 2017/0232193 | A1* | 8/2017 | Gargano | A61M 5/1723 |
| | | | | 604/891.1 |
| 2019/0035499 | A1* | 1/2019 | Daya | G16H 20/13 |
| 2019/0125454 | A1* | 5/2019 | Stokes | A61B 34/10 |
| 2019/0125457 | A1* | 5/2019 | Parihar | A61B 34/10 |
| 2019/0172572 | A1* | 6/2019 | Piron | H04B 1/385 |
| | | | | 455/41.2 |
| 2019/0198166 | A1* | 6/2019 | Errico | G16H 20/13 |

OTHER PUBLICATIONS

Camara et al., "Security and privacy issues in implantable medical devices: A comprehensive survey," Apr. 24, 2015, pp. 1-2. (Year: 2015).*

Ivan, D., "Moving Toward a Blockchain-based Method for the Secure Storage of Patient Records," Aug. 2016, pp. 3-6. (Year: 2016).*

Rosier et al. "An ontology-based annotation of cardiac implantable electronic devices to detect therapy changes in a national registry." IEEE journal of biomedical and health informatics 19.3 (2015): 971-978.

Michael et al. "Applications of human transponder implants in mobile commerce." This conference paper was originally published as Michael, K and Masters, A, Applications of human transponder implants in mobile commerce, in Proceedings of the 8th World Multiconference on Systemics, Cybernetics and Informatics, Orlando, Florida, Jul. 18-21, 2004, 5, 505-512.

Mel, et al. "The NIST Definition of Cloud Computing". Recommendations of the National Institute of Standards and Technology. Nov. 16, 2015.

* cited by examiner

SECURITY SCANNING FOR PASSENGERS WITH MEDICAL DEVICES

TECHNICAL FIELD

The present invention relates generally to a security scanning method, and more particularly, but not by way of limitation, to a system, method, and computer program product for receiving a communication of information from a medical device associated with a traveler for triggering the sending of the information to the device and storing the information in a blockchain.

SUMMARY

In an exemplary embodiment, the present invention can provide a computer-implemented security scanning method, the method including receiving a communication of information from a medical device associated with a traveler via a security device and triggering a sending of the information to the device and storing the information in a blockchain.

One or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION

Figure 1:
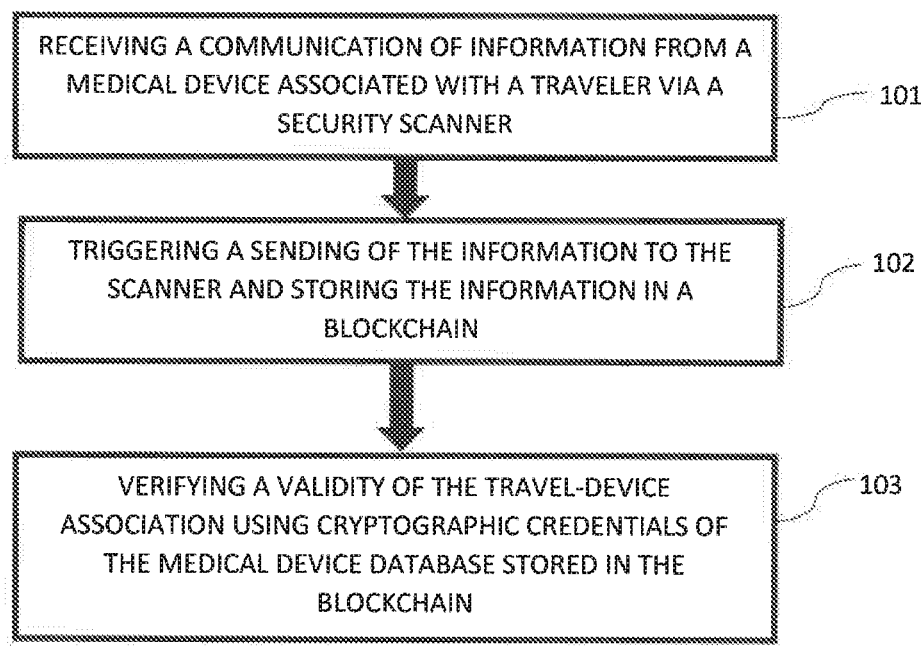
FIG. 1 exemplarily shows a high-level flow chart for a security scanning method 100 according to an embodiment of the present invention.

The invention will now be described with reference to FIGS. 1-4, in which like reference numerals refer to like parts throughout. It is emphasized that, according to common practice, the various features of the drawing are not necessarily to scale. On the contrary, the dimensions of the various features can be arbitrarily expanded or reduced for clarity.

By way of introduction of the example depicted in FIG. 1, an embodiment of a security scanning method 100 according to the present invention can include various steps interacting with a security device for receiving a communication of information from a medical device associated with a traveler (e.g., an airport, a train, a cruise ship, etc.) and for triggering the sending of the information to the scanner and storing the information in a blockchain.

Figure 2:
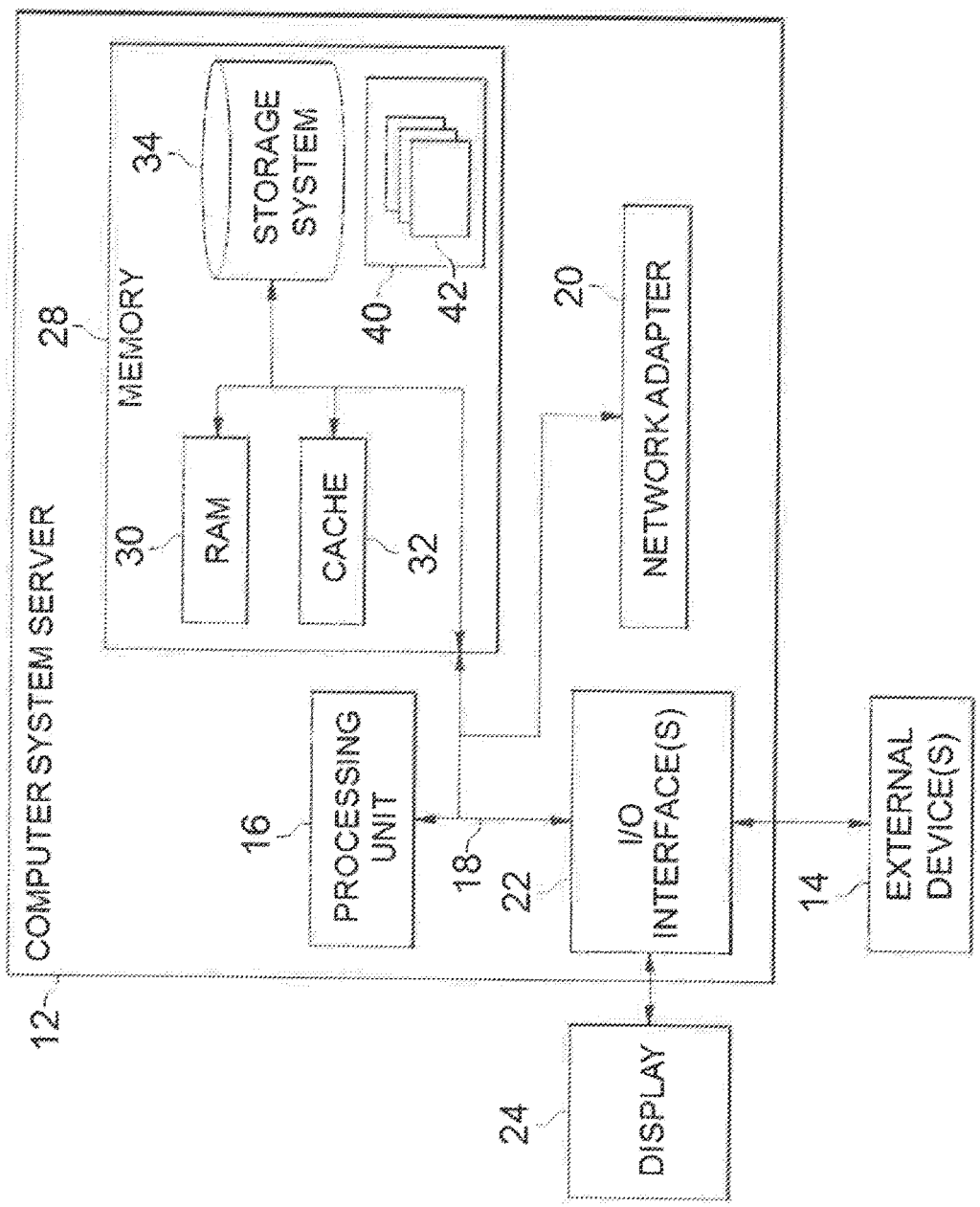
FIG. 2 depicts a cloud-computing node 10 according to an embodiment of the present invention.

By way of introduction of the example depicted in FIG. 2, one or more computers of a computer system 12 according to an embodiment of the present invention can include a memory 28 having instructions stored in a storage system to perform the steps of FIG. 1.

Thus, a security scanning method 100 according to an embodiment of the present invention may act in a more sophisticated, useful and cognitive manner, giving the impression of cognitive mental abilities and processes related to knowledge, attention, memory, judgment and evaluation, reasoning, and advanced computation. In other words, a "cognitive" system can be said to be one that possesses macro-scale properties—perception, goal-oriented behavior, learning/memory and actions generally recognized as cognitive.

Although one or more embodiments may be implemented in a cloud environment 50 (see e.g., FIG. 3), it is nonetheless understood that the present invention can be implemented outside of the cloud environment, Referring generally to the method of FIG. 1, at/near a security device (or the like), a communication of information from a medical device associated with a traveler is received (i.e., in step 101), and information is triggered to be sent to the security device and to a blockchain (i.e., step 102). In one embodiment described below assuming an airport environment, the airport security device can obtain a unique identifier from the active medical device, the airport security device can obtain an identifier from the traveler. The airport security device can then use the plurality of identifiers to look up for an association stored in a distributed, trustworthy electronic ledger (i.e., blockchain) having been previously set to securely transmit private information and the airport security device can verify the validity of the travel-device association using cryptographic credentials of the medical provider that established this association, which are also stored in the blockchain.

Additional verification of the medical device can be provided by the supplier of the medical device, the medical professional that installed the device, or the like (i.e., via step 103).

Depending on risk, context, or other triggers, the nature of the content added to the block of the blockchain may change, and the frequency of addition to the block may change. The blockchain is used, in part, to provide a convenient and distributed tamper-proof record. If risk is deemed to be too high (e.g., for whatever reason, including security alerts in the news, traveler cohort, airport location, etc.), then additional information may be automatically written to the blockchain, and it may automatically be written more frequently (e.g. slightly more information may be written regarding the device characteristics every second while near a scanner). Thus, the blockchain can be updated on-the-fly (e.g., dynamically) so as to monitor real-time health of the traveler and update the same.

The method can further be configured as an opt-in service. If a user does not wish to use this service, more traditional means of security checking may be employed.

The medical device may be any of a prosthetic, wearable pump, wearable pouch, oxygen tank, implantable cardiac pacemakers, implantable defibrillators, leads, electrodes, adaptors for implantable cardiac pacemakers and defibrillators, implantable neuro stimulator systems, brachytherapy, haemodynamic support, cochlear implants, implantable infusion pumps and accessories, implantable glucose monitors, micro electro-mechanical systems (MEMS), implantable gastric stimulators, neuroprosthetics, transcutaneous vagus nerve stimulators (tVNS), smart pills, etc.

The device itself may optionally provide tactile feedback or feedback via body sound-transmission schemes to indicate to a user that a transmission to the security device has successfully or not successfully taken place. For example, a medical device may vibrate or send audio sound through the body to a person's ear, using the method described below.

The information transmitted to the airport security device and to the growing blockchain may include any of a device ID, person ID, device state, device type, etc. For privacy and other reasons, some or all of this information may be additionally encrypted. For example, every person or medical device may have an associated blockchain that grows with information as a person travels. The blockchain provides additional encryption that can protect travelers.

The aforementioned triggering of information sending may be based on proximity (e.g. proximity of device to a scanner).

Also, the device itself may optionally provide tactile or other feedback to a user to confirm the receipt of information associated with the person or device. For example, some part of a device might safely vibrate for a half-second, which the user may feel.

Moreover, the device may communicate to the user to confirm sending and/or receipt of a message (or to make a request of the user) using an innovative sound transmission system that transmits sound wirelessly to the ears without making any other noise outside the body. That is, the system can utilize the human body as a sound transmission medium. The human body is a nonlinear medium and the nonlinear characteristic is the basis of the theorem for the system. When two ultrasonic waves with different frequencies are transmitted into the body, the difference frequency signal between the two original ultrasonic waves is generated during the propagation process and audible to a user. A single sideband amplitude modulation (SSB AM) method can be used as a modulation scheme. The SSB AM method can minimize the noise which occurs in the process of generating audible sound. To make a SSB AM modulator with a higher degree of accuracy, digital weaver modulation (DWM) method is adopted. DWM method enables a sharp cutoff filter to be implemented without increasing computational complexity in the DSP. An Equalizer filter which compensates the distortions in the ultrasonic transducer is also designed. If the proposed system is applied to the human body, sound transmission may be possible without a cable line being required as in conventional earphones.

Although the embodiments described herein are generally related to security devices, the invention is not limited thereto. That is, the invention can also can help caregivers ensure their elderly relatives are treated with dignity, yet expedite the process of getting an elderly through airport security safely. The elderly may have hearing aids, an exterior component of a cochlear implants, etc. They may also have surgically implanted devices such as artificial hips or aneurysm clips.

Passengers with pacemakers and defibrillators should not go through the metal detectors, and an alert may be provided alerting information just before a person might be using a metal detector. Many travelers rely on personal medical electronic devices (PMEDs) (e.g., pacemakers, neurostimulators, implantable cardio defibrillators, insulin pumps, blood glucose monitors, etc.).

In one embodiment, the invention may help facilitate medical information communication that facilitates seamless communication between a remote system and one or more medical devices implanted within a body of a patient or worn on the body. If desired, the scanner may actually receive physiological data from a medical device implanted within a body of a patient or worn on the body. This may optionally help health experts understand the state of a person about to take a long flight.

In another embodiment, the system may be optionally notified when a person enters a secure gate area, boards or leaves an aircraft, etc.

In another embodiment, the security system (e.g. scanner) may convey information regarding a receipt of a communication from the medical device. For example, an indicator on the scanning device may turn a specific color.

The information conveyed from the medical device may also be used to provide instructions to, for example, Transportation Safety Administration (TSA) agents for how to best handle or deal with a person with such a device.

In another embodiment, the information about a person, coupled with their location (e.g. through tracking the phone or boarding card, as the person passes through various checkpoints), may be used to help optimize and route the passengers through the terminal and assign them to check points. Often there is more than one checkpoint, and this way the checkpoints can navigate the checks for the person with the medical device.

In another embodiment, information about the traveler, their context, and cognitive state, coupled with the medical condition may be further used (once verified through blockchain) to customize the service (e.g. way of speaking, guidance, etc.) provided to the person at the checkpoint (e.g. a first time, elderly traveler, traveling unaccompanied, etc.).

Additionally a CAPTCHA-like mechanism may be embedded in the medical device and be used for a "digital handshake" between the end user and the check point person. CAPTCHAs may be based on the user's condition and/or route, etc.)

Based on the type of the implant in the person, the communication between the device and the scanner can inform the scanner that the person should not be scanned to prevent harm to the person. For example, certain heart-associated implants should not be scanned, and if a scenario is identified that a person with such implant attempts to go through the scanner (because of a confusion, disorientation, etc.), the scanner will turn itself off to prevent harm to the person. This is a secure operation due to the use of blockchain.

In another embodiment, the information about the implant can be used for the scanner as part of the signature of that implant, and not only inform the scanner that the implant is present (as confirmed by the secure block chain) but also can use the implant image (preloaded, could be a template image for the hip prosthetics, etc.) overlaid on the scanned image of the person. The overlay image may use a different color for the implant than other objects that appear on the scanner to reduce any confusion.

Optionally, travelers can enjoy the benefits of travelling by signing, with the TSA, a smart contract, which is a computer protocol intended to facilitate, verify, or enforce the negotiation or performance of a contract, and storing the contract in the blockchain. For example, travelers can provide their details to the TSA prior to their travel and create contracts with the TSA that allows them to travel without being checked. Essentially, a traveler's details and other information about health conditions can be digitally written as part of a smart contract that TSA approves. Once the TSA approves the requirements, the TSA and the traveler can sign the contract for the service and the contract gets stored in the blockchain. Now, when the traveler travels, his or her contracts get digitally executed via blockchain technology and the information is shared across all the nodes that are part of the blockchain. This has several important benefits.

The techniques above can identify non-approved members with respect to approved members. Without the approval, there is a possibility of intruders making an illegal entry with illegal possession.

Secondly, the invention described herein is dynamic in nature. For example, where a traveler had to switch to a new machine or medicines. Based on the new aspect, the traveler can send this information via a mobile application or just by calling. The contract is updated and shared across all nodes that validate the authenticity of the traveler.

Based on the smart contract execution, trust models can be built that rank the travelers based on how they perform. For example, if every time a traveler contract gets executed successfully, then the TSA will have a better trust than the travelers whose contracts do not get executed successfully. Based on higher trust, the TSA gets to decide whether to perform verification or screening or not.

In one embodiment, a traveler can sign a smart contract with the airport security. The smart contracts are temper proof and can be dynamically updated ensuring the benefits for both travelers and airport security.

Thereby, the invention can provide for a better way to handle individuals with medical devices at security checkpoints.

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 2, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring now to FIG. 2, a computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further described below, memory 28 may include a computer program product storing one or program modules 42 comprising computer readable instructions configured to carry out one or more features of the present invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may be adapted for implementation in a networking environment. In some embodiments, program modules 42 are adapted to generally carry out one or more functions and/or methodologies of the present invention.

Computer system/server 12 may also communicate with one or more external devices 14 such as a keyboard, a pointing circuit, other peripherals, such as display 24, etc., and one or more components that facilitate interaction with computer system/server 12. Such communication can occur via Input/Output (I/O) interface 22, and/or any circuits (e.g., network card, modem, etc.) that enable computer system/server 12 to communicate with one or more other computing circuits. For example, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 3:
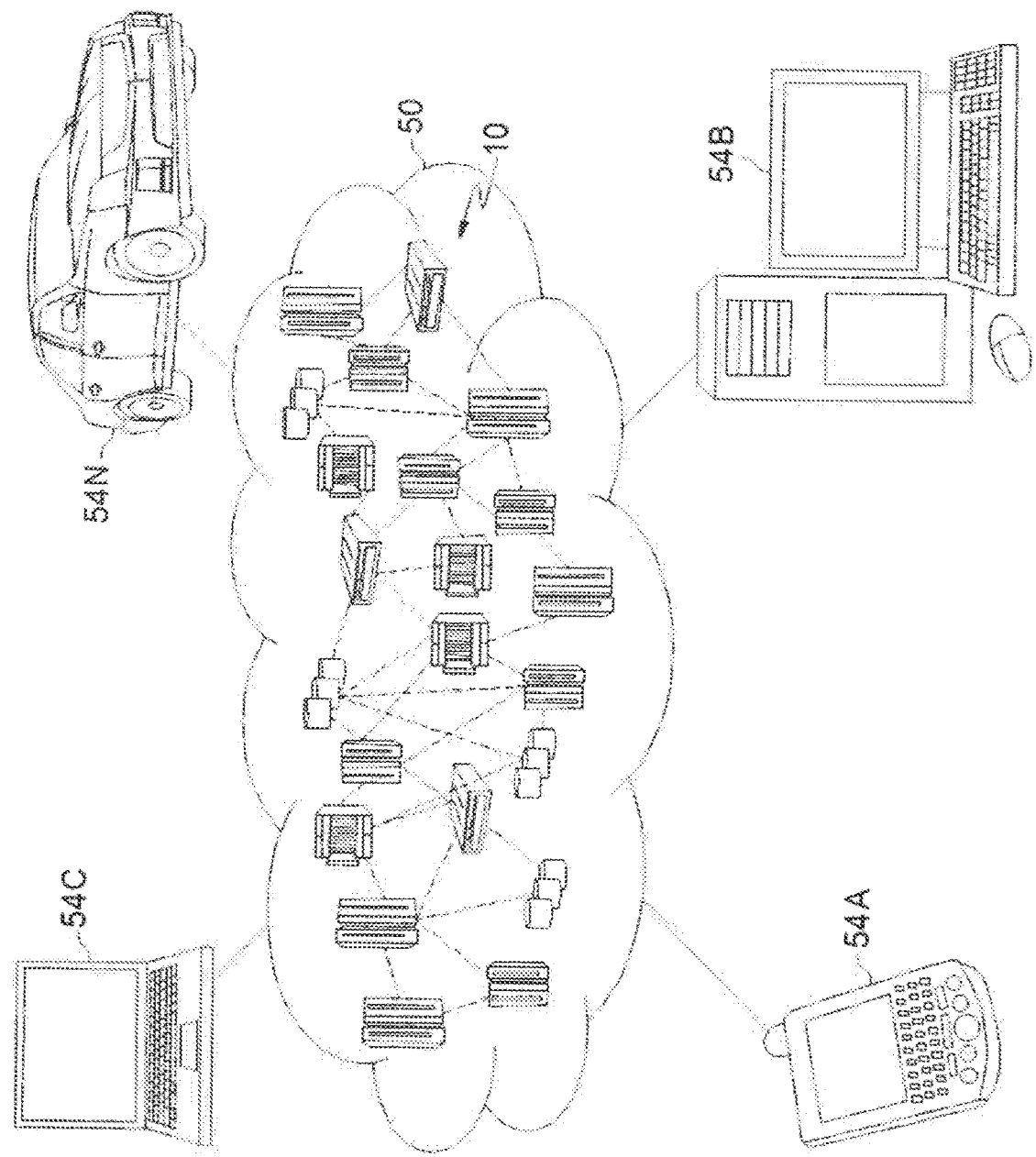
FIG. 3 depicts a cloud-computing environment 50 according to an embodiment of the present invention.

Referring now to FIG. 3, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 3 are intended to be illustrative only and that computing nodes 10 and cloud computing environment 50 can communicate with any type of computerized circuit over any type of network and/or network addressable connection (e.g., using a web browser).

Figure 4:
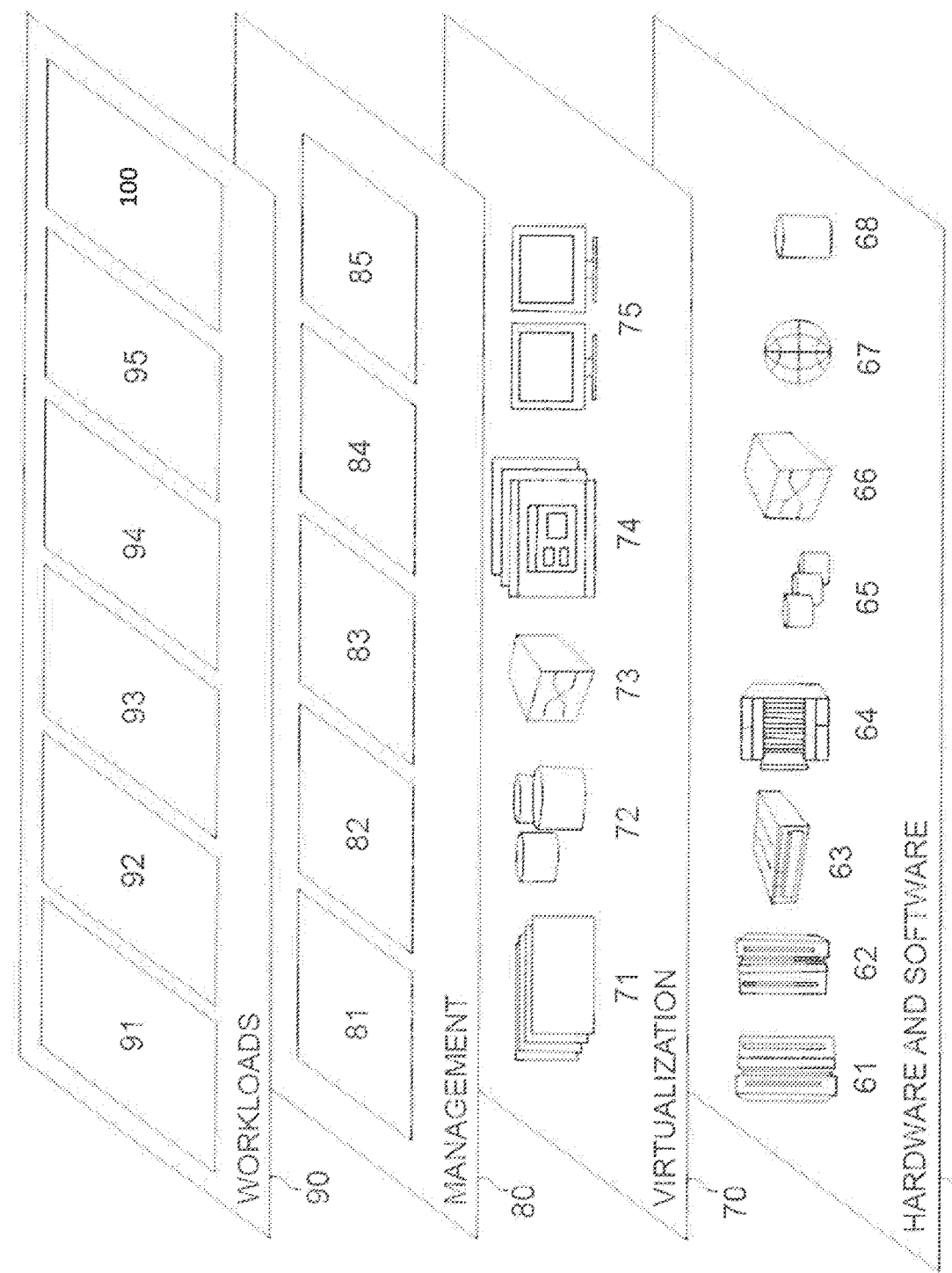
FIG. 4 depicts abstraction model layers according to an embodiment of the present invention.

Referring now to FIG. 4, an exemplary set of functional abstraction layers provided by cloud computing environment 50 (FIG. 43) is shown. It should be understood in advance that the components, layers, and functions shown in FIG. 4 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and security scanning method 100 in accordance with the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a liber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented security scanning method, the method comprising:
    receiving, via a security device:
        a communication of information, via the security device, from a medical device associated with a traveler, the information including a unique identifier of the medical device obtained from a medical device database; and
        an identifier from the traveler, via the security device;
    storing the identifier of the traveler in a blockchain;
    triggering a sending of both of the information and the identifier of the traveler to the security device and storing the information in the blockchain; and
    providing instructions to a security device operator, based on the information in the blockchain, for a handling of the traveler according to a guidance for handling the medical device with the security device,
    wherein, in the triggering, the security device determines if the unique identifier matches the identifier of the traveler by looking up an association between the unique identifier and the identifier of the traveler stored in the blockchain.

2. The computer-implemented method of claim 1, the method further comprising verifying a validity of the traveler-device association using cryptographic credentials of the medical device database, which are stored in the blockchain,
    wherein the traveler is flagged if a medical condition associated with the medical device is unsafe for travel.

3. The computer-implemented method of claim 1, wherein the handling instructions are provided depending on a risk associated with the medical device and a context, a nature of content added to the blockchain changes, and a frequency of an addition to the blockchain changes.

4. The computer-implemented method of claim 1, wherein the medical device includes at least one of:
    a prosthetic;
    a wearable pump;
    a wearable pouch;
    an oxygen tank;
    an implantable cardiac pacemaker;
    an implantable defibrillator;
    a lead, electrode, and adaptor for the implantable cardiac pacemakers and defibrillator;
    an implantable neuro stimulator system;
    a brachytherapy;
    haemodynamic support;
    a cochlear implant;
    an implantable infusion pump and accessory;
    an implantable glucose monitor;
    a micro electro-mechanical system (MEMS);
    an implantable gastric stimulator;
    neuroprosthetics;
    a transcutaneous vagus nerve stimulation (tVNS); and
    a smart pill.

5. The computer-implemented method of claim 1, wherein the medical device provides one of tactile feedback and feedback via a body sound-transmission scheme to indicate to a user that a transmission to the security device has successfully taken place.

6. The computer-implemented method of claim 1, wherein the information transmitted to the security device and the blockchain includes at least one of:
    a device ID;
    a person ID;
    a device state; and
    a device type.

7. The computer-implemented method of claim 1, wherein the triggering of the sending is based on a proximity of the medical device of the traveler to the security device.

8. The computer-implemented method of claim 1, wherein the traveler executes a smart contract with the security device, the smart contract being a tamper-proof and dynamically updated ledger ensuring a benefit for the traveler and security device.

9. The computer-implemented method of claim 1, embodied in a cloud-computing environment.

10. A computer program product for security scanning, the computer program product comprising a computer readable storage medium having program instructions embodied therewith, the program instructions executable by a computer to cause the computer to perform:
   receiving, via a security device:
      a communication of information, via the security device, from a medical device associated with a traveler, the information including a unique identifier of the medical device obtained from a medical device database; and
      an identifier from the traveler, via the security device;
   storing the identifier of the traveler in a blockchain;
   triggering a sending of both of the information and the identifier of the traveler to the security device and storing the information in the blockchain; and
   providing instructions to a security device operator, based on the information in the blockchain, for a handling of the traveler according to a guidance for handling the medical device with the security device,
   wherein, in the triggering, the security device determines if the unique identifier matches the identifier of the traveler by looking up an association between the unique identifier and the identifier of the traveler stored in the blockchain.

11. The computer program product of claim 10, the method further comprising verifying a validity of the traveler-device association using cryptographic credentials of the medical device database, which are stored in the blockchain.

12. The computer program product of claim 10, wherein the medical device includes at least one of:
   a prosthetic;
   a wearable pump;
   a wearable pouch;
   an oxygen tank;
   an implantable cardiac pacemaker;
   an implantable defibrillator;
   a lead, electrode, and adaptor for the implantable cardiac pacemakers and defibrillator;
   an implantable neuro stimulator system;
   a brachytherapy;
   haemodynamic support;
   a cochlear implant;
   an implantable infusion pump and accessory;
   an implantable glucose monitor;
   a micro electro-mechanical system (MEMS);
   an implantable gastric stimulator;
   neuroprosthetics;
   a transcutaneous vagus nerve stimulation (tVNS); and
   a smart pill.

13. The computer program product of claim 10, wherein the medical device provides one of tactile feedback and feedback via a body sound-transmission scheme to indicate to a user that a transmission to the security device has successfully taken place.

14. The computer program product of claim 10, wherein the information transmitted to the security device and the blockchain includes at least one of:
   a device ID;
   a person ID;
   a device state; and
   a device type.

15. The computer program product of claim 10, wherein the triggering of the sending is based on a proximity of the medical device of the traveler to the security device.

16. The computer program product of claim 10, wherein the traveler executes a smart contract with the security device, the smart contract being a tamper-proof and dynamically updated ledger ensuring a benefit for the traveler and security device.

17. A security scanning system, said system comprising:
   a processor; and
   a memory, the memory storing instructions to cause the processor to perform:
      receiving, via a security device:
         a communication of information, via the security device, from a medical device associated with a traveler, the information including a unique identifier of the medical device obtained from a medical device database; and
         an identifier from the traveler, via the security device;
      storing the identifier of the traveler in a blockchain;
      triggering a sending of both of the information and the identifier of the traveler to the security device and storing the information in the blockchain; and
      providing instructions to a security device operator, based on the information in the blockchain, for a handling of the traveler according to a guidance for handling the medical device with the security device,
      wherein, in the triggering, the security device determines if the unique identifier matches the identifier of the traveler by looking up an association between the unique identifier and the identifier of the traveler stored in the blockchain.

18. The system of claim 17, embodied in a cloud-computing environment.

* * * * *